United States Patent
Harris et al.

(10) Patent No.: US 8,961,720 B2
(45) Date of Patent: Feb. 24, 2015

(54) METHOD FOR GUIDING AND BONDING STRANDS TO A SUBSTRATE

(71) Applicant: Nordson Corporation, Westlake, OH (US)

(72) Inventors: Michael W. Harris, Cumming, GA (US); Alan Ramspeck, Cumming, GA (US)

(73) Assignee: Nordson Corporation, Westlake, OH (US)

(*) Notice: Subject to any disclaimer, the term of this patent is extended or adjusted under 35 U.S.C. 154(b) by 155 days.

(21) Appl. No.: 13/684,844

(22) Filed: Nov. 26, 2012

(65) Prior Publication Data

US 2014/0144577 A1    May 29, 2014

(51) Int. Cl.
| | |
|---|---|
| *B05C 5/02* | (2006.01) |
| *B65H 57/16* | (2006.01) |
| *B05C 1/00* | (2006.01) |
| *B65H 57/04* | (2006.01) |
| *B65H 57/14* | (2006.01) |
| *A61F 13/15* | (2006.01) |
| *B29C 65/48* | (2006.01) |

(52) U.S. Cl.
CPC ............... *B05C 1/00* (2013.01); *B05C 5/0241* (2013.01); *B65H 57/04* (2013.01); *B65H 57/14* (2013.01); *B65H 57/16* (2013.01); *A61F 13/15593* (2013.01); *B29C 65/48* (2013.01)
USPC ............................. 156/178; 156/161; 156/436

(58) Field of Classification Search
CPC ...... B05C 5/0241; B65H 57/04; B65H 57/14; B65H 57/16; B65H 2701/319; A61F 13/15593
USPC .......... 156/161, 178, 179, 436, 494; 118/234, 118/325
See application file for complete search history.

(56) References Cited

U.S. PATENT DOCUMENTS

| | | | | |
|---|---|---|---|---|
| 5,525,175 | A * | 6/1996 | Blenke et al. ................. | 156/161 |
| 5,964,973 | A * | 10/1999 | Heath et al. ................... | 156/161 |
| 6,613,146 | B2 * | 9/2003 | Bolyard, Jr. .................. | 118/325 |
| 7,465,367 | B2 * | 12/2008 | Day .............................. | 156/161 |
| 7,578,882 | B2 | 8/2009 | Harris et al. | |
| 2010/0024987 | A1 * | 2/2010 | Saine et al. .................. | 156/439 |
| 2012/0258246 | A1 * | 10/2012 | Saine et al. ............... | 427/207.1 |

OTHER PUBLICATIONS

Valco Melton, Hot Melt Systems by Valco melton, Engineered for Tomorrow, Brochure, 2010 English Edition, 8 pgs.
Melton, S.L., Bat Nozzles, Blown Adhesive Technology, undated, 1 pg.
Valco Melton, Bat Series, Independent Air Heater Applicator, Brochure, undated, 2 pgs.
Valco Melton, The Hotmelt Alternative, Brochure, 2005, 13 pgs.

* cited by examiner

*Primary Examiner* — Michael Tolin
(74) *Attorney, Agent, or Firm* — Wood, Herron & Evans, L.L.P.

(57) ABSTRACT

A method of bonding first and second strands onto a substrate traveling along a machine direction in a plane of travel. The method includes moving the first and second strands in the machine direction relative to a nozzle having a nozzle body with first and second liquid discharge passages, and first and second side-by-side notches. The first and second strands are guided for movement by engaging closed ends of the respective first and second notches. Open ends of the first and second notches are oriented or directed non-perpendicular to the plane of travel of the substrate. Liquid adhesive is dispensed onto the first and second strands from the liquid discharge passages and the first and second strands are bonded to the substrate.

15 Claims, 8 Drawing Sheets

METHOD FOR GUIDING AND BONDING STRANDS TO A SUBSTRATE

TECHNICAL FIELD

The present invention generally relates to methods for dispensing liquid adhesive onto individual strands within a group of strands.

BACKGROUND OF THE INVENTION

Many reasons exist for dispensing liquid, such as hot melt adhesives, in the form of a thin filament or fiber with a controlled pattern. Conventional patterns used in the past have been patterns involving a spiraling of the filament by impacting the filament with jets of process air. The nozzles used to achieve this spiraling effect can be obtained from Nordson Corp., Westlake, Ohio under the trademarks Controlled Fiberization™, CF™, or Summit™. Controlled fiberization techniques are especially useful for accurately covering a wider region of a substrate with adhesive dispensed as single filaments or as multiple side-by-side filaments from nozzle passages having small diameters, such as on the order of 0.010 inch to 0.060 inch. This is especially useful on very narrow substrates, such as on elastic strands, e.g., Lycra®, used in the manufacture of disposable diapers or other disposable products. Other adhesive filament dispensing techniques and apparatus have been used for producing a non-overlapping, oscillating pattern of adhesive on a substrate or, in other words, a stitching pattern in which the adhesive moves back-and-forth generally in a zig-zag form on the substrate.

Various types of nozzles or die tips, such as those of the type described above, have been used to dispense adhesive onto one or more elastic strands. For such applications, the strand or strands typically need to be guided at specific spaced apart positions as the adhesive is discharged onto the strand or strands. Even a single strand needs to be guided and stabilized to ensure accurate placement of the adhesive on the strand. For this purpose, strand guides may take the form of rollers that are fixed to the dispensing module or some other fixed structure, or alternatively they may take the form of a notched structure integrated with or otherwise mounted proximate the nozzle. An exemplary dispensing module having an integrated strand guide is disclosed in U.S. Pat. No. 7,578,882, assigned to the assignee of the present invention, and the disclosure of which is hereby expressly incorporated by reference herein in its entirety. In this form of strand guide, one or more notches respectively guide one or more elastic strands as the strand or strands move in the machine direction or, in other words, lengthwise along a manufacturing line. While integrated notched structures work acceptably for two or more strands running in parallel, a minimum spacing is required between the strands. The minimum spacing is designed to ensure that the flow of adhesive and process air intended for one strand does not interfere with the adhesive and process air intended for an adjacent strand. The spacing requirement imposes constraints on the design of products, such as diapers, that may require elastic strands to be spaced from one another by distances smaller than those allowed by current nozzles.

It would therefore be desirable to provide a method of dispensing adhesive onto individual strands within a group of strands in a manner that achieves the ability to even more closely space the strands on an adhered substrate than the existing technology.

SUMMARY

In one embodiment, the invention provides a method of bonding first and second strands onto a substrate traveling along a machine direction in a plane of travel. The method generally involves moving the first and second strands along the machine direction relative to a nozzle having a nozzle body including first and second liquid discharge passages, and first and second side-by-side notches each having an open end for receiving one of the first or second strands and a closed end for engaging and guiding one of the first or second strands. Movement of the first and second strands is guided in the machine direction with the first and second strands respectively engaging the closed ends of the respective first and second notches and with the open ends of the first and second notches directed or oriented non-perpendicular to the plane of travel of the substrate. Liquid adhesive is dispensed onto the first and second strands from the respective first and second liquid discharge passages, and the first and second strands are bonded to the substrate. As examples, the adhesive may be discharged from the nozzle, in a non-contact manner, as a filament that travels through the air before contacting the strand, or may be directly applied to the strand, such as in a contacting or slot-coating manner.

In more specific aspects, the nozzle body extends along a nozzle body axis that is non-perpendicular to the plane of the travel of the substrate. Further, the nozzle body is oriented such that the nozzle body axis is generally parallel to the plane of travel of the substrate. The method further comprises supporting the first and second strands respectively along first and second guiding notches of a roller. The first guiding notch has a first depth relative to a circumferential surface of the roller. The second guiding notch has a second depth, different from the first depth, relative to the circumferential surface of the roller. The roller rotates about a roller axis that is generally perpendicular to the nozzle body axis. The open ends of the first and second notches extend parallel to the plane of travel of the substrate in more specific embodiments. Bonding of the first and second strands onto the substrate further comprises bonding the first and second strands on the substrate at a spacing between each other in the range of about 0 mm to about 5 mm or, more specifically, a range of about 0 mm to about 2.5 mm. The nozzle body further includes a discharge end surface, which is the endmost surface that includes the open ends of the notches. The closed end of the second notch is farther from the discharge end surface than is the closed end of the first notch.

In another aspect of the method, the first and second strands are moved along the machine direction while the first and second strands lie in a first plane and at a first spacing between the first and second strands. The liquid adhesive is dispensed onto the first and second strands from the nozzle onto the first and second strands while the first and second strands lie in the first plane, and at a second spacing between the first and second strands which is less than the first spacing. The method further comprises redirecting at least one of the first or second strands out of the first plane while moving the first and second strands from the nozzle to the substrate, and bonding the first and second strands onto the substrate while the first and second strands are in the plane of travel and at the second spacing on the substrate.

Various additional features of the invention will become more readily apparent to those of ordinary skill in the art upon review of the following detailed description of the illustrative embodiments, taken in conjunction with the accompanying drawings.

DETAILED DESCRIPTION OF ILLUSTRATIVE EMBODIMENTS

Figure 1:
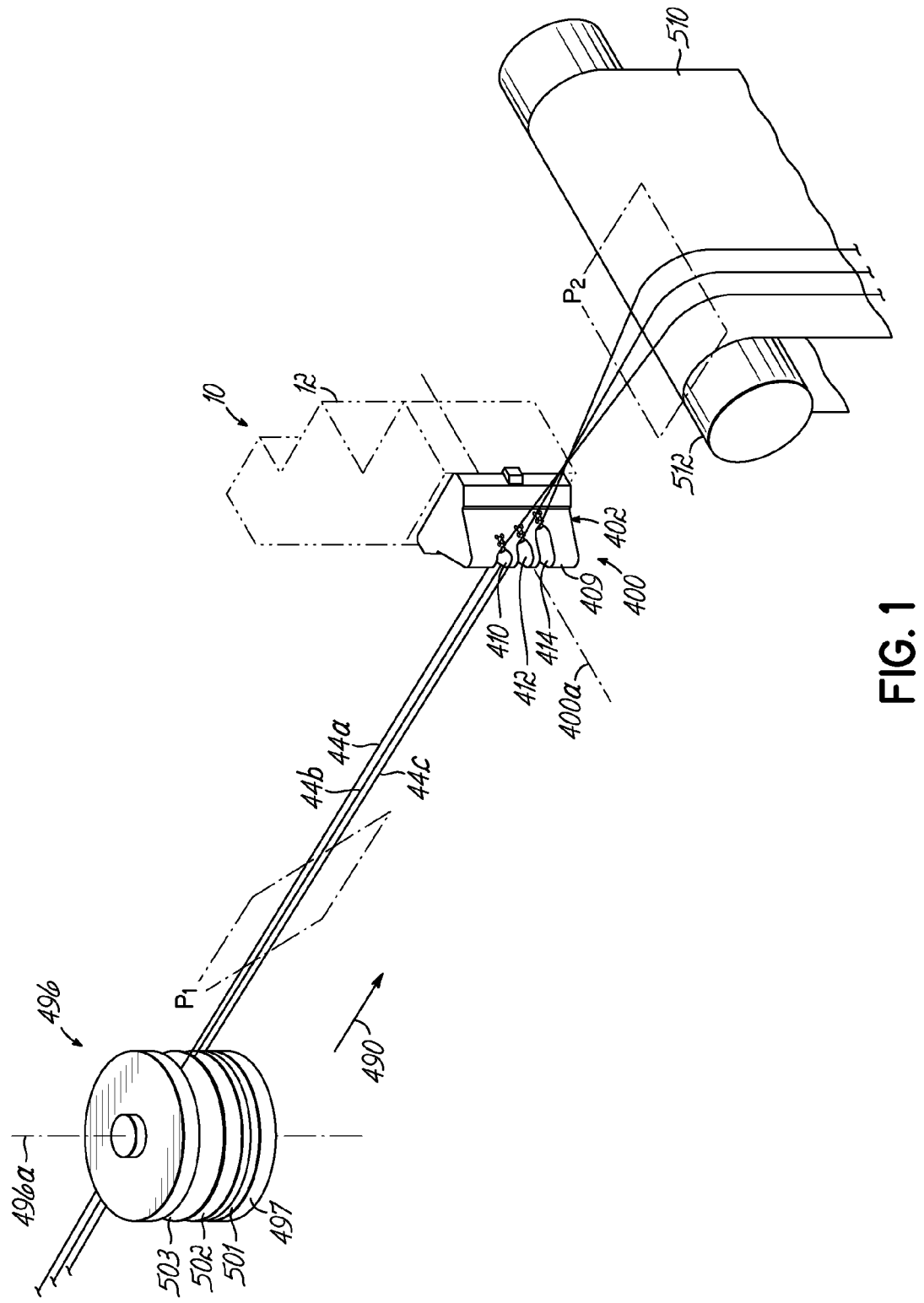
FIG. 1 is a perspective view illustrating an exemplary system and process for dispensing liquid onto strands of substrate material.

FIG. 1 illustrates an exemplary process for dispensing adhesive, onto three strands of substrate material, such as elastic strands. The process illustrated in FIG. 1 includes guiding of the three strands 44a, 44b, 44c from an upstream source (not shown) of strand material. As used herein, the terms "upstream" and "downstream" refer to directions relative to the machine direction i.e., the direction of travel of the strands 44a, 44b, 44c, generally designated by arrow 490 in FIG. 1. The strands 44a, 44b, 44c are guided toward nozzle 400 by a guide roller 496 located upstream of nozzle 400. The roller 496 rotates about an axis of rotation 496a. The axis of rotation 496a is generally perpendicular to the nozzle body axis 400a, and in the illustrated embodiment, also generally perpendicular to each of the notch axes 410d, 412d, 414d. The guide roller 496 has three circumferentially extending, spaced notches 501, 502, 503, each of which receives therein one of the strands 44a, 44b, 44c. In the illustrated embodiment, the notches 501, 502, 503 have depths that are different from one another i.e., with depth being defined as the distance from the circumferential surface 497 of the guide roller 496 to each of the closed ends of the notches 501, 502, 503. Notably in this embodiment, the depth of each of the notches 501, 502, 503 is chosen to respectively correspond to the depth of each of the notches 410, 412, 414 of nozzle 400. This feature facilitates guiding of the strands 44a, 44b, 44c into the notches 410, 412, 414. More specifically, the design of the notches 501, 502, 503 of guide roller 496 directs the strands 44a, 44b, 44c to travel in a generally constant plane $P_1$ in the span between the guide roller 496 and the nozzle 400.

The strands 44a, 44b, 44c then advance through the nozzle 400 with the strands 44a, 44b, 44c following respective paths of travel that differ from one another in their respective spacing from the discharge end surface 409 of nozzle 400. As the strands 44a, 44b, 44c exit the notches 410, 412, 414, the nozzle 400 dispenses respective filaments of liquid adhesive onto the surfaces of the strands 44a, 44b, 44c in a non-contact manner, thereby coating them with the liquid. In the illustrated embodiment, the liquid adhesive dispensed by the nozzle 400 is a hot melt adhesive. The strands 44a, 44b, 44c, with adhesive on their surfaces, are then directed toward a substrate 510 which may be a non-woven web, a film web, or a paper web, for example, and which is in turn supported by an idler roller or a driven roller 512. The strands 44a, 44b, 44c are then bonded onto the substrate 510 by virtue of the adhesive deposited on the strand surfaces. The idler roller or driven roller 512 is oriented, in this embodiment, such that the substrate 510 lies in a plane of travel $P_2$ at the location of bonding with the strands 44a, 44b, 44c. As the strands 44a, 44b, 44c exit the nozzle 400, at least two are gradually reoriented or redirected so as to attain respective orientations conforming with the plane of travel $P_2$ of substrate 510.

The orientation of the idler roller or driven roller 512, guide roller 496, and nozzle 400 relative to one another in the embodiment of FIG. 1 is intended to be illustrative rather than limiting, insofar as other relative orientations (not shown) are contemplated. For example, the orientation of the guide roller 496 and nozzle 400 may be such that they guide the strands 44a, 44b, 44c to travel in a plane that is different from the exemplary plane $P_1$ associated with the embodiment of FIG. 1. The orientations of the nozzle 400 and idler roller or driven roller 512 in FIG. 1 are such that the nozzle body axis 400a defines an angle of about 90 degrees relative to the direction of travel (arrow 490) of the strands 44a, 44b, 44c while being substantially parallel to the plane $P_2$ of the substrate 510.

It will also be understood from FIG. 1 that the open ends of the notches 410, 412, 414 are directed non-perpendicular to the plane of travel $P_2$. More specifically, in this embodiment, the open ends of the notches are each oriented in a direction generally parallel to the plane of travel $P_2$. It will be appreciated that other non-perpendicular orientations may be used instead. Such an orientation ensures the ability to achieve minimum desired spacing of the strands 44a, 44b, 44c on the substrate 510.

The strands 44a, 44b, 44c may be bonded onto the substrate 510 with a spacing between them in the range of about 0 mm to about 5 mm for example and, more specifically, in the range of about 0 mm to about 2.5 mm in some cases. This close spacing between the strands 44a, 44b, 44c is facilitated by the staggered design of the notches 410, 412, 414 (FIG. 3), as well as by the angled orientation of the nozzle 400 relative to plane $P_2$. More specifically, the spacing between strands 44a, 44b, 44c is a function of the difference in depth of the notches 410, 412, 414, and the angle of orientation of the nozzle 400. In addition, other factors that contribute to the close spacing between elastic strands 44a, 44b, 44c include, without limitation, the chosen supply (i.e., flow rate and direction) of process air and adhesive respectively out of the air outlets 460 and the liquid outlets 420, 422, 424. In that regard, for example the supply of process air may be chosen so as to define a cone of process air that is no wider than about 4 mm upon impacting the strands 44a, 44b, 44c. This relatively narrow cone of process air limits the interference of process air intended for one strand with process air intended for an adjacent strand, which thereby allows a design for nozzle 400 in which the difference in notch depth is relatively small, thus further minimizing the spacing of the strands 44a, 44b, 44c when the nozzle 400 is oriented at an angle (e.g., as in FIG. 1).

In another aspect of the exemplary orientation of FIG. 1, the illustrated arrangement of the nozzle 400 and idler roller or driven roller 512 is such that the strands 44a, 44b, 44c travel through the nozzle 400 along respective paths that are located at first, second, and third distances, different from one another, in the direction of the roller axis 496*a* (i.e., perpendicular to the nozzle body axis 400*a*). And, by virtue of the staggered design of the notches 410, 412, 414, the respective paths of travel of the strands 44*a*, 44*b*, 44*c* through the nozzle 400 are also located at distances from the discharge end surface 409 of the nozzle 400 that are different from one another. In addition to the above, the exemplary orientation of the nozzle 400 in FIG. 1 is such that the nozzle body axis 400*a* and all of the notch axes 410*d*, 412*d*, 414*d* are non-perpendicular and, more specifically in the illustrated embodiment, generally parallel to the plane $P_2$ of the substrate 510. It is contemplated, however, that any of the notch axes 400*a*, 410*d*, 412*d*, 414*d* (FIG. 6) may instead be oriented at some other angle (i.e., acute angle) relative to the plane $P_2$, and still fall within the spirit and scope of the present disclosure.

Those of ordinary skill in the art will readily appreciate that the embodiment illustrated in FIG. 1 is exemplary and in no way intended to be limiting, with variations being readily contemplated. For example, and without limitation, an alternative process may obviate a guide roller 496 having notches 501, 502, 503 of different depth, but may instead use a roller having notches of similar or even identical depth, or use no guide roller at all. In one of those alternative embodiments, an alternative guide roller may have notches of similar depth and be oriented, for example, at an angle such that the strands 44*a*, 44*b*, 44*c* define a plane of travel $P_1$ substantially similar to the plane $P_1$ of FIG. 1, between that alternative guide roller and the nozzle 400. That angle would be such that the axis of rotation of that alternative guide roller would be oriented at an acute angle relative to the nozzle body axis 400*a*.

Figure 2:
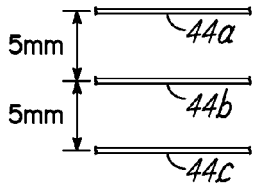
FIG. 2 is a schematic illustration of the strand spacing at three different points in the process.

FIG. 2 schematically illustrates the strand spacing at different points of the process illustrated in FIG. 1. More specifically, the top three blocks of FIG. 2 illustrate schematic side views of portions of the strands 44*a*, 44*b*, 44*c*, respectively, at a first position or location along the manufacturing line which is prior to engagement with the roller 496; at a second location or position which is just prior to and within the notches 410, 412, 414 of the nozzle 400; and at a third location or position which is on the substrate 510. The lower three blocks of FIG. 2 are respective top views of the strands at the same positions in the manufacturing process of FIG. 1. It will be appreciated that upstream of the roller 496, the strands may have relatively wide spacing, such as 5 mm, as shown, and may be essentially vertically oriented as indicated by the top view of the Pre-Roller position, i.e., the lower left hand box of FIG. 2. By the time the strands 44*a*, 44*b*, 44*c* enter the notches 410, 412, 414, the spacing between the strands 44*a*, 44*b*, 44*c* is reduced, for example, to 2 mm. This is illustrated in the two center or Pre-Nozzle boxes of FIG. 2. At this stage of the manufacturing process, the strands 44*a*, 44*b*, 44*c* are spaced vertically by 2 mm and are also spaced horizontally, or relative to the plane of travel $P_2$, by 2 mm. By the time the strands 44*a*, 44*b*, 44*c* reach the substrate 510, at least two of the strands have been redirected or reoriented such that, as depicted in the upper right hand or On Substrate box of FIG. 2, the strands 44*a*, 44*b*, 44*c* lie in the plane $P_2$ and, as shown in the top view (i.e., lower right hand box), are spaced by 2 mm. Therefore, it will be understood that the strands 44*a*, 44*b*, 44*c* are redirected from a vertical or near vertical plane that contains them prior to the guide roller 496 to a horizontal or near horizontal plane of travel $P_2$ when they are adhered to the substrate 510.

Figure 3:
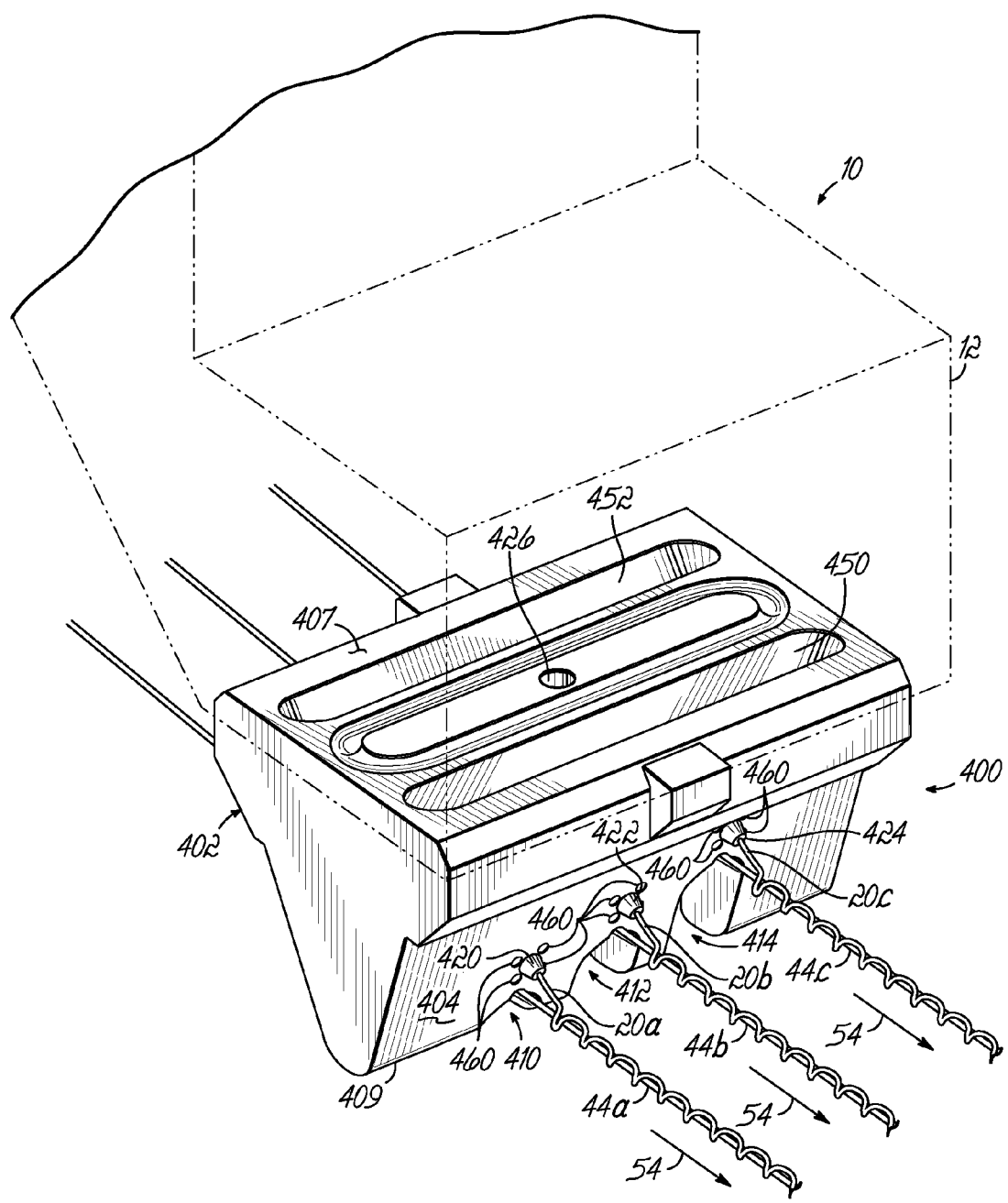
FIG. 3 is a perspective view of a dispensing module including an illustrative nozzle or die tip usable in the system of FIG. 1.

FIG. 3 illustrates an exemplary dispensing module or applicator 10 according to one embodiment of the present invention. Dispensing module 10 has a main body 12 (in broken lines) that is configured for selective attachment of one of various nozzles or dies, as more fully described in U.S. Pat. No. 6,619,566 which is assigned to the assignee of the present invention, and the disclosure of which is hereby expressly incorporated by reference herein in its entirety. Main body 12 may include fasteners (not shown) for securing module 10 to a suitable support, such as a manifold (not shown) that supplies liquid, such as hot melt adhesive, to module 10. Module 10 may be of the on/off type and includes an internal valve structure for selectively dispensing liquid, such as hot melt adhesive or other viscous liquid typically formed from polymeric material, in the form of one or more filaments. A suitable module structure is part no. 309637 commercially available from Nordson Corporation, of Westlake, Ohio, which is the assignee of the present invention.

FIG. 3 further illustrates an exemplary nozzle 400 coupled to the main body 12 of dispensing module 10. Nozzle 400 receives liquid and pressurized air from the main body 12 and dispenses respective filaments of liquid material 20*a*, 20*b*, 20*c* in controlled patterns onto respective strands 44*a*, 44*b*, 44*c* of substrate material moving relative to the nozzle 400, generally in the direction of arrows 54. The pattern of the filament may take any desired form suitable for the application. While not shown, it is contemplated that the dispensing module 10 may include a quick disconnect mechanism for permitting releasable coupling of various types of nozzles such as nozzle 400, or any other type of releasable or fixed coupling components, so as to facilitate replacement of nozzles from the main body 12 of module 10.

Figure 4:
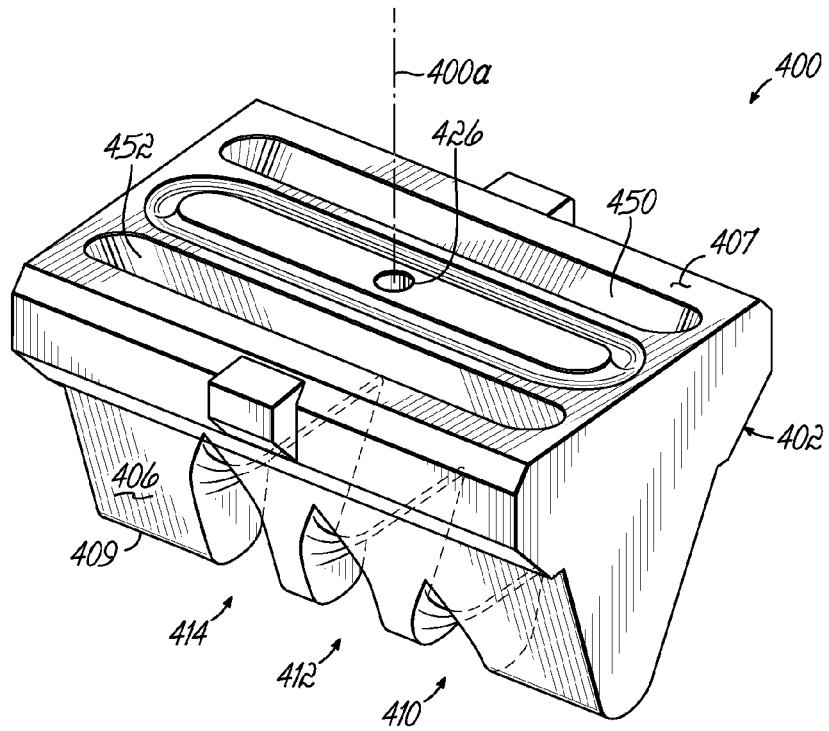
FIG. 4 is a rear perspective view of the nozzle of FIG. 3.
Figure 5:
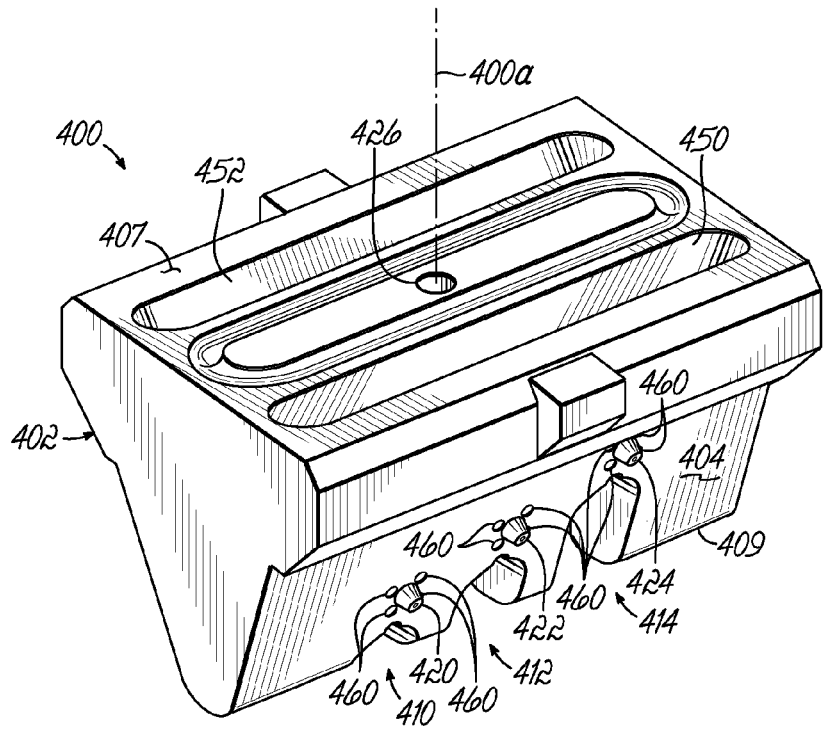
FIG. 5 is a front perspective view of the nozzle of FIGS. 3 and 4.
Figure 6:
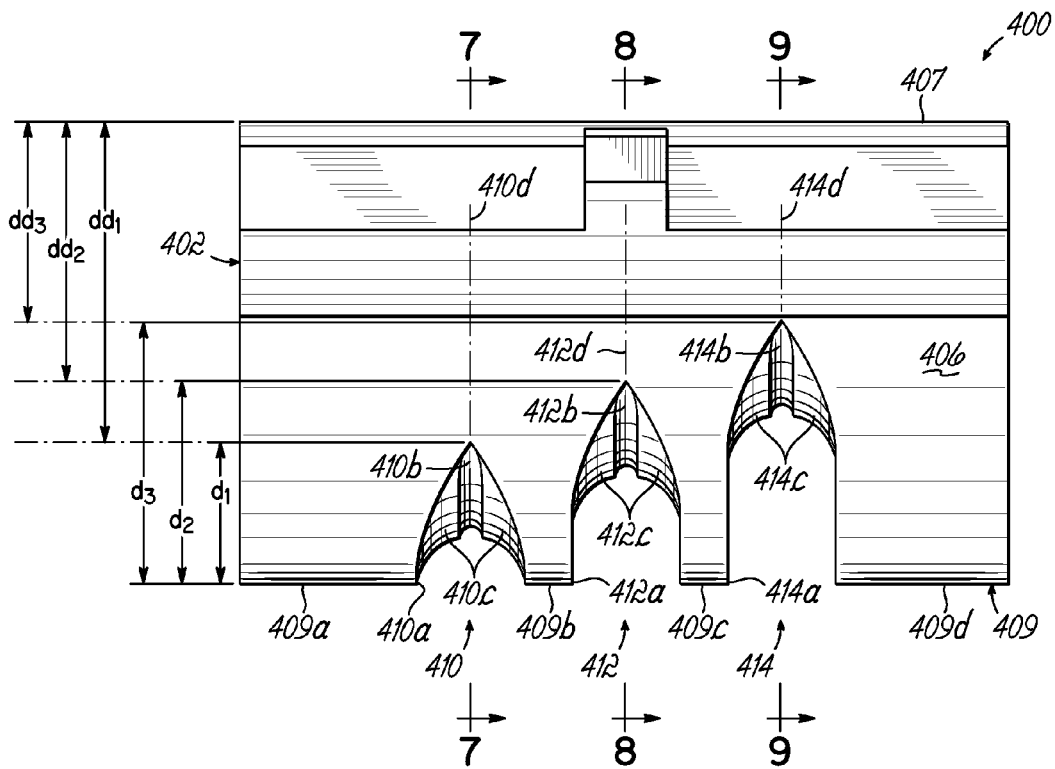
FIG. 6 is a rear elevational view of the nozzle of FIGS. 3-5.
Figure 7:
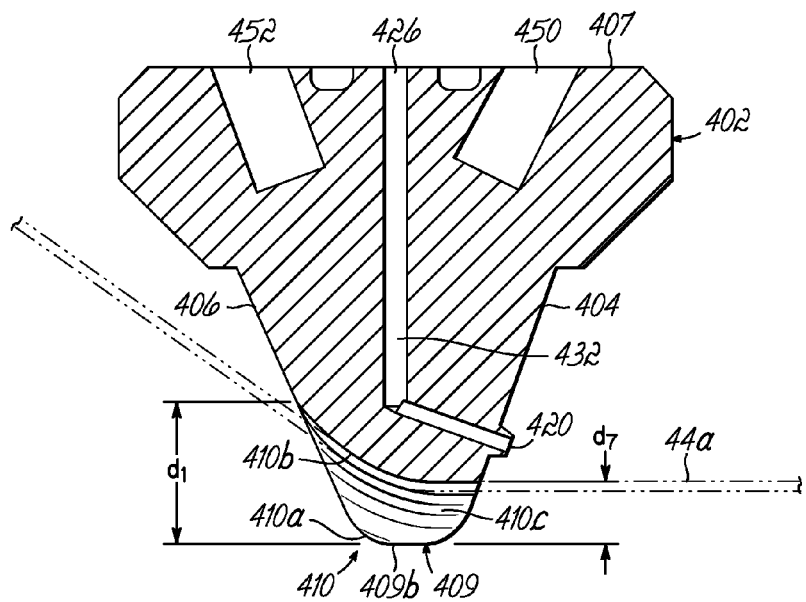
FIG. 7 is a transverse cross-sectional view of the nozzle of FIG. 6, taken generally along line 7-7 of FIG. 6.
Figure 8:
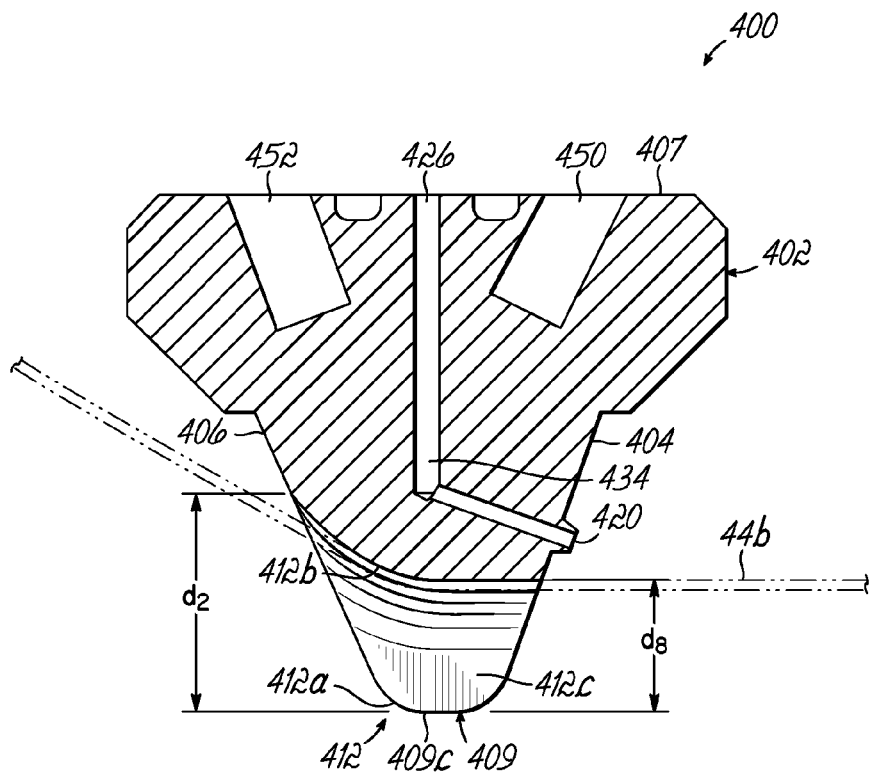
FIG. 8 is a transverse cross-sectional view of the nozzle of FIG. 2-6, taken generally along line 8-8 of FIG. 6.
Figure 9:
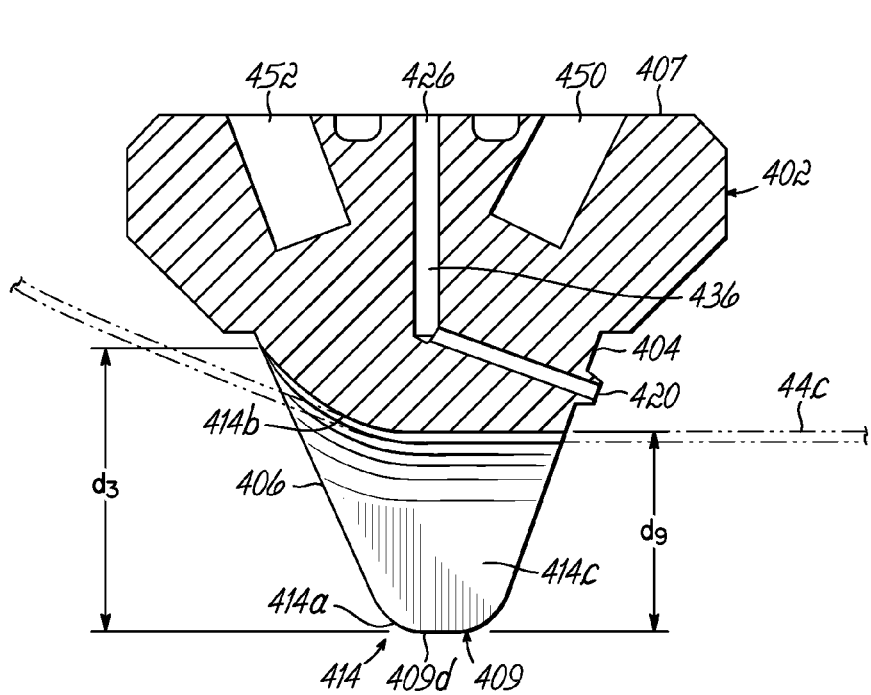
FIG. 9 is a transverse cross-sectional view of the nozzle of FIG. 6, taken generally along line 9-9 of FIG. 6.

Referring to FIGS. 4-6, details of the nozzle 400 are illustrated. For ease of explanation and understanding, like reference numerals throughout the figures refer to like structures. Nozzle 400 has a nozzle body 402 extending along a nozzle body axis 400*a*, formed from a suitably chosen metal such as brass, and having front and rear surfaces 404, 406, an upper surface 407, and a distal, lower surface 409. In the illustrated embodiment, the upper surface 407 also defines a mounting surface of the nozzle 400, which is suitable for coupling engagement with the module 10, as shown in FIG. 3, for example. Nozzle 400 includes a strand guide in the form of an integrated notched structure having a plurality of generally V-shaped notches 410, 412, 414, each configured to guide a respective strand 44*a*, 44*b*, 44*c* of substrate past liquid and air outlets of nozzle body 402. Nozzle 400 also includes liquid outlets 420, 422, 424, respectively receiving a liquid such as hot melt adhesive from one or more liquid inlets 426 and along respective liquid discharge passages 432, 434, 436 (FIGS. 7-9). The notches 410, 412, 414 comprise a strand guide integrated into the nozzle 400. It will be appreciated that notches 410, 412, 414 may instead be formed in a guide that is fastened to a nozzle body or to the main body of a dispenser, or otherwise suitably mounted proximate the nozzle. The liquid outlets 420, 422, 424 are located at the front surface 404, respectively above each of the apexes of notches 410, 412, 414. Respective process air discharge passages (not shown), direct process air from one or more air inlet ports such as recesses 450, 452 formed into upper surface 407. The process air discharge passages (not shown) extend through the nozzle body 402 and exit at respective process air outlets 460 on the front surface 404.

In the illustrated embodiment, the first liquid outlet 420 and a corresponding first set of process air outlets 460 are located at an axial distance (i.e., the distance measured in a direction parallel to nozzle body axis 400*a* and parallel to respective main axes of the notches) from the apex of notch 410 that is similar to the corresponding axial distances of the liquid outlets 422, 424 and air outlets 460 for each of the other two notches 412, 414, although this is only intended to be exemplary rather than limiting. In that regard, it is contemplated that an alternative nozzle may have a first notch in which the corresponding liquid outlet 420 and/or air outlets 460 are located at a first axial distance from the apex of that first notch, and a second notch in which the corresponding liquid outlet 420 and/or air outlets 460 are located at a second axial distance from the apex of that second notch, which is different than the first axial distance.

Figure 6A:
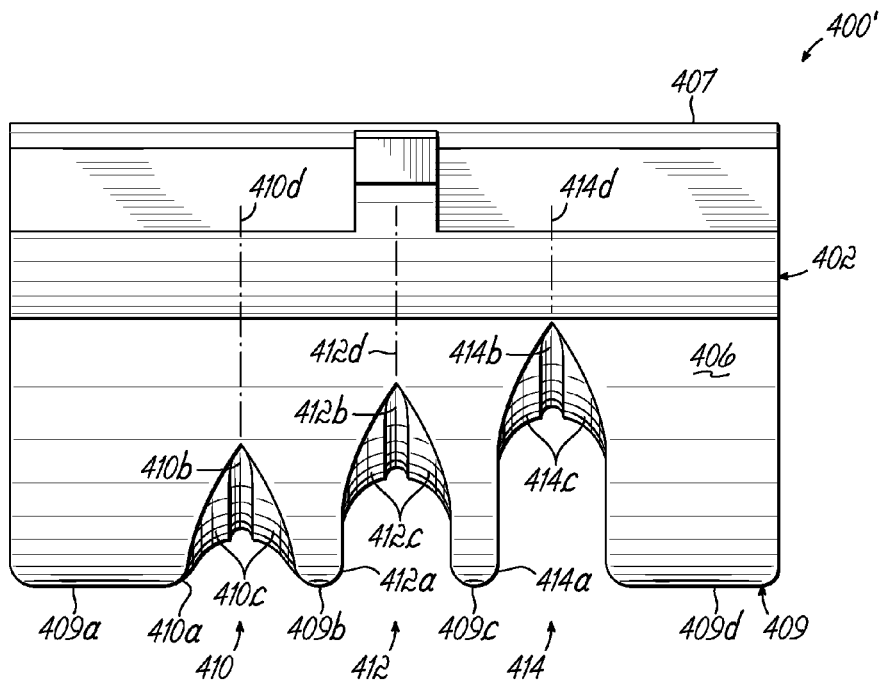
FIG. 6A is a rear elevational view similar to FIG. 6, illustrating an alternative embodiment of a nozzle.
Figure 6B:
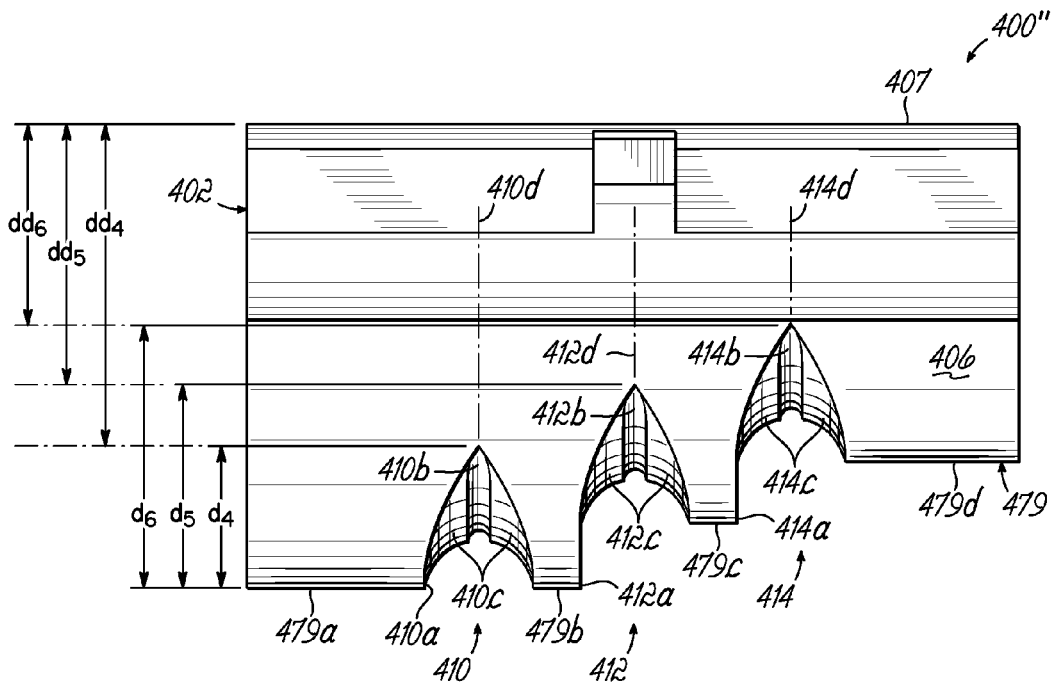
FIG. 6B is a rear elevational view of yet another alternative embodiment of a nozzle.

With particular reference to FIGS. 6, 6A and 6B, each of the notches 410, 412, 414 is defined by an open end 410a, 412a, 414a, a closed end 410b, 412b, 414b, and a pair of converging opposed sidewalls 410c, 412c, 414c, with the closed ends 410b, 412b, 414b being located between the pairs of sidewalls 410c, 412c, 414c. In the exemplary embodiment shown in FIG. 6, the lower surface 409 is made up of four, generally flat coplanar surface sections 409a, 409b, 409c, 409d, adjacent the open ends 410a, 412a, 414a, though this is not intended to be limiting insofar as variations are contemplated.

One variation of a nozzle 400' is illustrated in FIG. 6A, for example, in which the two outer surface sections 409a, 409d have beveled corners, and in which the two inner surface sections 409b, 409c are generally rounded rather than planar.

With continued reference to FIG. 6, each of the notches 410, 412, 414 extends along a respective notch axis 410d, 412d, and 414d that is, in this embodiment, parallel to the nozzle body axis 400a of nozzle body 402. The notches 410, 412, 414 have depths that are different from one another. This allows for closer spacing of the guided strands 44a, 44b, 44c because it ensures that there is no interference between adjacent jets of pattern air. Specifically, the first notch 410 has its closed end 410b located at a first distance $d_1$ from the lower surface 409, and particularly from the surface section 409a, and the second notch 412 has its closed end 412b located at a second distance $d_2$ from the lower or discharge end surface 409, particularly from the surface section 409a, with the second distance $d_2$ being larger than the first distance $d_1$. The third notch 414 has its closed end 414b located at a third distance $d_3$ from the lower surface 409, particularly from the surface section 409a, with the third distance $d_3$ being larger than both the first and second distances $d_1$, $d_2$. All three of the above-discussed distances $d_1$, $d_2$, $d_3$ are measured in a direction that is parallel to the nozzle body axis 400a. In addition, in the illustrated embodiment the first, second, and third closed ends 410b, 412b, 414b are located at different distances $dd_1$, $dd_2$, $dd_3$ from the mounting surface 407 of nozzle body 402.

Those of ordinary skill in the art will readily appreciate that variations of the nozzle are contemplated. For example, an alternative embodiment of a nozzle may have only two notches or a number of notches in excess of three. In another embodiment (not shown), a nozzle may have notches in which their respective notch axes 410d, 412d, 414d are not all parallel to one another and/or in which one or more of the notch axes 410d, 412d, 414d is/are not parallel to the nozzle body axis 400a of nozzle body 402. In yet another embodiment (not shown), two of the notches 410, 412, 414 may have similar depths, or the deepest notch may be located in a position other than that shown in FIG. 6.

Another embodiment of a nozzle 400" is illustrated in FIG. 6B. Nozzle 400" has a stepped lower surface 479, having four lower surface sections 479a, 479b, 479c, 479d that lie in respective planes different from one another. In this embodiment, in which like reference numerals refer to like features of FIG. 6, the first notch 410 has its closed end 410b located at a first distance $d_4$ from the discharge end surface 479a, and the second notch 412 has its closed end 412b located at a second distance $d_5$ from the discharge end surface 479a, with the second distance $d_5$ being larger than the first distance $d_4$. The third notch 414 has its closed end 414b located at a third distance $d_6$ from the discharge end surface 479a, with the third distance $d_6$ being larger than both, the first and second distances $d_4$, $d_5$. All three of the above-discussed distances $d_4$, $d_5$, $d_6$ associated with FIG. 6B are measured in a direction that is parallel to the nozzle body axis 400a of nozzle body 402 and measured with respect to the endmost surface or discharge end surface 479a. In addition, in the illustrated embodiment the first, second, and third closed ends 410b, 412b, 414b are located at different distances $dd_4$, $dd_5$, $dd_6$ from the mounting surface 407 of nozzle body 402.

With reference to FIGS. 7-9, respective cross-sectional views of nozzle 400 illustrate guiding of three strands 44a, 44b, 44c of substrate material, such as elastic strands. FIG. 7, in particular, shows guiding of a first one of the strands 44a, with the strand 44a exiting the guide at a first distance $d_7$ from the plane in which discharge end surface 409 lies, with the distance $d_7$ being determined by the depth of the first notch 410. FIG. 8 shows guiding of a second one of the strands 44b, with the strand 44b exiting the guide at a second distance $d_8$ from the plane in which discharge end surface 409 lies, with the distance $d_8$ being determined by the depth of the second notch 412. FIG. 9 shows guiding of a third one of the strands 44c, with the strand 44c exiting the guide at a third distance $d_9$ from the plane in which discharge end surface 409 lies, with the distance $d_9$ being determined by the depth of the third notch 414. The distances $d_7$, $d_8$, $d_9$ are different from one another. This difference in the respective distances $d_7$, $d_8$, $d_9$ at which the three stands 44a, 44b, 44c are located relative to the nozzle body 402 permit the strands to be spaced at minimum distances from one another. Also, the vertical spacing (relative to the orientation in FIGS. 7-9) of the strands 44a, 44b, 44c prevents interference of the liquid (e.g., adhesive) and corresponding process air intended for one strand from interfering with the liquid and corresponding process air intended for an adjacent strand. This vertical spacing can also prevent adhesive intended for one strand from contacting (e.g., adhesively-coating) an adjacent strand.

Figure 10:
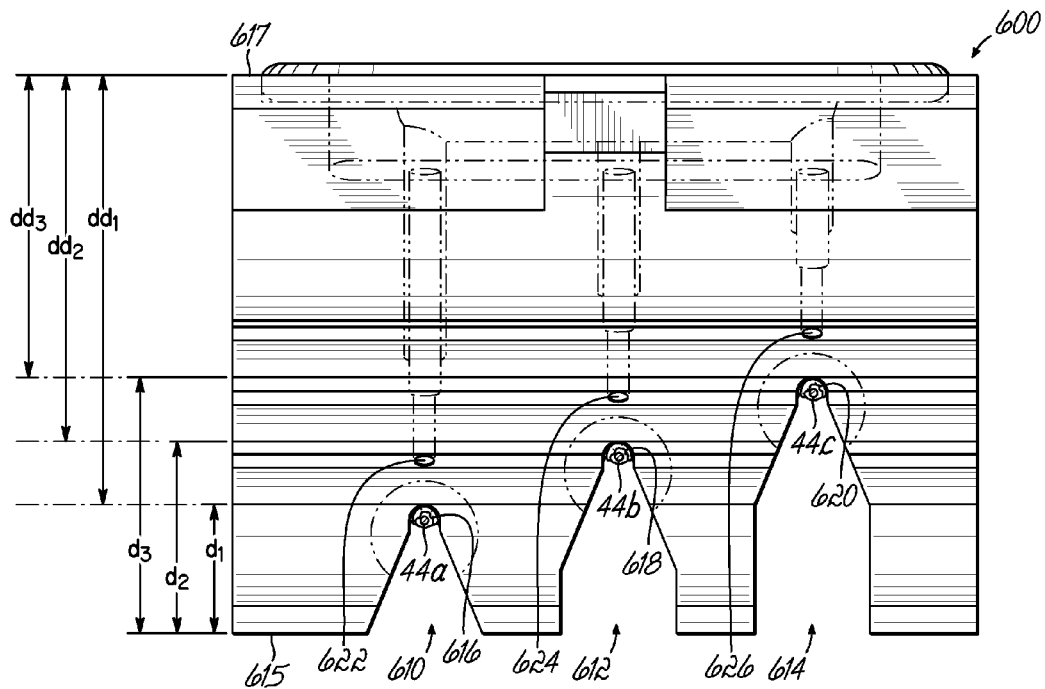
FIG. 10 is a front elevational view of a nozzle useful in the methods of this invention, and according to another illustrative embodiment.

FIG. 10 illustrates another embodiment of a nozzle 600 used in the methods according to this invention. This nozzle is a modified form of a nozzle constructed according to the disclosure of U.S. Patent Application Publication No. US2012/0258246, ("the '246 application), assigned to the assignee of the present invention and the entire disclosure of which is hereby incorporated by reference herein. The modifications to the nozzle are with regard to the notches 610, 612, 614. Similar to the previously described embodiments herein, the notches 610, 612, 614 are modified to have different depths. Therefore, the distances $d_1$, $d_2$, $d_3$ (measured from the discharge end surface 615) and $dd_1$, $dd_2$, and $dd_3$ (measured from the nozzle mounting surface 617) are present as described with regard to the embodiments illustrated in FIG. 6. This nozzle 600 dispenses adhesive 616, 618, 620 within each notch 610, 612, 614 to thereby coat each strand 44a, 44b, 44c as per the disclosure in the '246 application. The adhesive is therefore applied in a contact manner directly to the strands 44a, 44b, 44c. The adhesive 616, 618, 620 is then spread onto the respective strands 44a, 44b, 44c using process air discharged from respective process air outlets 622, 624, 626 associated with each notch 610, 612, 614. The nozzle 600 of FIG. 10 is used in methods according to this invention as previously described with regard to the nozzles 400, 400', 400" that dispense adhesive filaments, discussed above. In this regard, the nozzle 600 may replace the nozzles 400, 400', 400", shown and described with regard to the system and method of FIG. 1.

Figure 11:
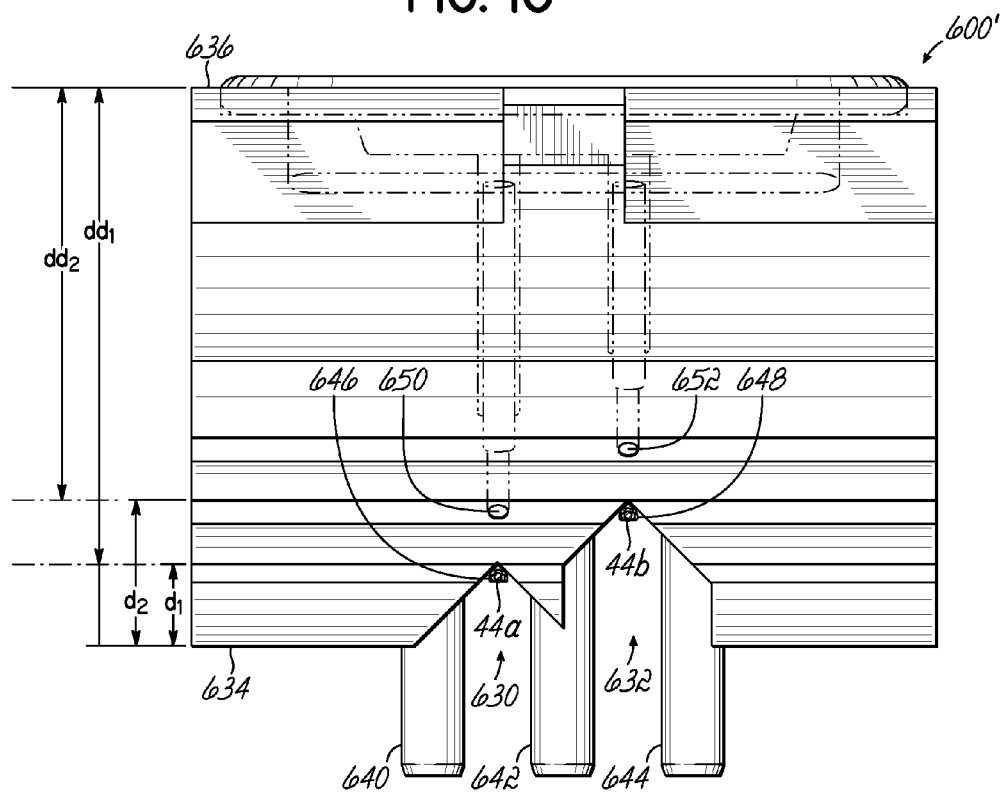
FIG. 11 is a front elevational view of a nozzle useful in the methods of this invention, and according to another illustrative embodiment.

FIG. 11 illustrates another alternative nozzle 600' used in the methods according to this invention. This nozzle 600' is another modified form of a nozzle constructed in accordance with the above incorporated '246 application and available as the Allegro™ elastic attachment nozzle from Nordson Corp., Westlake, Ohio. Nozzle 600' includes first and second notches 630, 632 receiving first and second strands 44a, 44b for the same purposes and in the same methodology as described above. Again, the notches 630, 632 are respectively formed to have different depths $d_1$, $d_2$, from the discharge end surface 634 and different distances $dd_1$, $dd_2$, from the nozzle mounting surface 636. This nozzle 600' further includes strand guide posts 640, 642, 644 for the reasons discussed in the '246 application. As with the nozzle 600 discussed above with regard to FIG. 10, nozzle 600' dispenses adhesive 646, 648 within each notch 630, 632 and directly onto each strand 44a, 44b in a contact manner. The adhesive is then spread out onto each strand 44a, 44b using process air discharged from process air outlets 650, 652, as more fully described in the '246 application. Again, this nozzle 600' is used in the manners described above with regard to the previously discussed nozzle embodiments and may be substituted for the nozzles 400, 400', 400", 600 in the method and system described in connection with FIG. 1.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A method of bonding first and second strands onto a substrate traveling along a machine direction in a plane of travel, the method comprising:
    moving the first and second strands along the machine direction relative to a nozzle having a nozzle body including first and second liquid discharge passages, and first and second side-by-side notches each having an open end for receiving one of the first or second strands and a closed end for engaging and guiding one of the first or second strands;
    guiding movement of the first and second strands in the machine direction with the first and second strands respectively engaging the closed ends of the respective first and second notches and with the open ends of the first and second notches oriented in a direction non-perpendicular to the plane of travel of the substrate;
    supporting the first and second strands respectively along first and second guiding notches, wherein the first guiding notch has a first depth and the second guiding notch has a second depth, different from the first depth;
    dispensing liquid adhesive onto the first and second strands from the respective first and second liquid discharge passages; and
    bonding the first and second strands to the substrate.

2. A method of bonding first and second strands onto a substrate traveling along a machine direction in a plane of travel, the method comprising:
    moving the first and second strands along the machine direction relative to a nozzle having a nozzle body including first and second liquid discharge passages, and first and second side-by-side notches each having an open end for receiving one of the first or second strands and a closed end for engaging and guiding one of the first or second strands, wherein the nozzle body extends along a nozzle body axis that is non-perpendicular to the plane of the travel of the substrate;
    guiding movement of the first and second strands in the machine direction with the first and second strands respectively engaging the closed ends of the respective first and second notches and with the open ends of the first and second notches directed non-perpendicular to the plane of travel of the substrate;
    supporting the first and second strands respectively along first and second guiding notches, wherein the first guiding notch has a first depth and the second guiding notch has a second depth, different from the first depth;
    dispensing liquid adhesive onto the first and second strands from the respective first and second liquid discharge passages; and
    bonding the first and second strands to the substrate.

3. A method of bonding first and second strands onto a substrate traveling along a machine direction in a plane of travel, the method comprising:
    moving the first and second strands along the machine direction relative to a nozzle having a nozzle body including first and second liquid discharge passages, and first and second side-by-side notches each having an open end for receiving one of the first or second strands and a closed end for engaging and guiding one of the first or second strands, wherein the nozzle body further includes a discharge end surface and the closed end of the second notch is farther from the discharge end surface than is the closed end of the first notch;
    guiding movement of the first and second strands in the machine direction with the first and second strands respectively engaging the closed ends of the respective first and second notches and with the open ends of the first and second notches directed non-perpendicular to the plane of travel of the substrate;
    dispensing liquid adhesive onto the first and second strands from the respective first and second liquid discharge passages; and
    bonding the first and second strands to the substrate.

4. A method of bonding first and second strands onto a substrate traveling along a machine direction in a plane of travel, the method comprising:
    moving the first and second strands along the machine direction relative to a nozzle having a nozzle body including first and second liquid discharge passages, and first and second side-by-side notches each having an open end for receiving one of the first or second strands and a closed end for engaging and guiding one of the first or second strands;
    guiding movement of the first and second strands in the machine direction with the first and second strands respectively engaging the closed ends of the respective first and second notches and with the open ends of the first and second notches oriented in a direction non-perpendicular to the plane of travel of the substrate;
    supporting the first and second strands respectively along first and second guiding notches of a roller, wherein the first guiding notch has a first depth relative to a circumferential surface of the roller, and the second guiding notch has a second depth, different from the first depth, relative to the circumferential surface of the roller;

rotating the roller about a roller axis that is generally perpendicular to the direction that the open ends of the first and second notch axes are oriented;

dispensing liquid adhesive onto the first and second strands from the respective first and second liquid discharge passages; and bonding the first and second strands to the substrate.

5. The method of claim 4, wherein the open ends of the first and second notches extend parallel to the plane of travel of the substrate.

6. The method of claim 4, wherein bonding of the first and second strands onto the substrate further comprises:
bonding the first and second strands on the substrate at a spacing between each other in the range of about 0 mm to about 5 mm.

7. The method of claim 4, wherein bonding of the first and second strands onto the substrate further comprises:
bonding the first and second strands on the substrate at a spacing between each other in the range of about 0 mm to about 2.5 mm.

8. The method claim 4, wherein the first and second strands are moved along the machine direction while the first and second strands lie in a first plane and at a first spacing between the first and second strands, and the liquid adhesive is dispensed onto the first and second strands from the nozzle onto the first and second strands while the first and second strands lie in the first plane, and at a second spacing between the first and second strands which is less than the first spacing, and the method further comprises:
redirecting at least one of the first or second strands out of the first plane while moving the first and second strands from the nozzle to the substrate; and
bonding the first and second strands onto the substrate while the first and second strands are in the plane of travel and at the second spacing on the substrate.

9. The method of claim 8, further comprising:
moving the first and second strands toward the roller along the machine direction and at the first spacing; and
guiding the first and second strands with the roller upstream of the nozzle, with a rotational axis of the roller oriented generally perpendicular to the plane of travel and with the first and second strands at the second spacing.

10. The method of claim 8, wherein bonding of the first and second strands onto the substrate further comprises:
bonding the first and second strands on the substrate at a spacing between each other in the range of about 0 mm to about 5 mm.

11. The method of claim 8, wherein bonding of the first and second strands onto the substrate further comprises:
bonding the first and second strands on the substrate at a spacing between each other in the range of about 0 mm to about 2.5 mm.

12. The method of claim 4, wherein dispensing the liquid adhesive further comprises:
dispensing the adhesive onto the first and second strands in a non-contact manner.

13. The method of claim 4, wherein dispensing the liquid adhesive further comprises:
dispensing the adhesive onto the first and second strands in a contact manner.

14. A method of bonding first and second strands onto a substrate traveling along a machine direction in a plane of travel, the method comprising:
moving the first and second strands along the machine direction relative to a nozzle having a nozzle body including first and second liquid discharge passages, and first and second side-by-side notches each having an open end for receiving one of the first or second strands and a closed end for engaging and guiding one of the first or second strands, wherein the nozzle body extends along a nozzle body axis that is non-perpendicular to the plane of the travel of the substrate;
guiding movement of the first and second strands in the machine direction with the first and second strands respectively engaging the closed ends of the respective first and second notches and with the open ends of the first and second notches directed non-perpendicular to the plane of travel of the substrate;
supporting the first and second strands respectively along first and second guiding notches of a roller, wherein the first guiding notch has a first depth relative to a circumferential surface of the roller, and the second guiding notch has a second depth, different from the first depth, relative to the circumferential surface of the roller;
rotating the roller about a roller axis that is generally perpendicular to the nozzle body axis,
dispensing liquid adhesive onto the first and second strands from the respective first and second liquid discharge passages; and
bonding the first and second strands to the substrate.

15. The method of claim 14, wherein the nozzle body is oriented such that the nozzle body axis is generally parallel to the plane of travel of the substrate.

* * * * *